United States Patent
Franck et al.

(10) Patent No.: US 7,666,210 B2
(45) Date of Patent: Feb. 23, 2010

(54) CONNECTION SYSTEM BETWEEN A SPINAL ROD AND A TRANSVERSE BAR

(75) Inventors: Bruno Franck, Argonay (FR); Mourad Ben Mokhtar, Paris (FR); David Ryan, Saint Cloud (FR)

(73) Assignee: Scient'x SA, Guyancourt (FR)

( * ) Notice: Subject to any disclaimer, the term of this patent is extended or adjusted under 35 U.S.C. 154(b) by 410 days.

(21) Appl. No.: 10/504,277

(22) PCT Filed: Feb. 11, 2003

(86) PCT No.: PCT/FR03/00425

§ 371 (c)(1),
(2), (4) Date: Jan. 10, 2005

(87) PCT Pub. No.: WO03/068087

PCT Pub. Date: Aug. 21, 2003

(65) Prior Publication Data

US 2005/0113831 A1    May 26, 2005

(30) Foreign Application Priority Data

Feb. 11, 2002    (FR) .................................. 02 01626

(51) Int. Cl.
*A61B 17/70*    (2006.01)
(52) U.S. Cl. .................... 606/250; 606/277; 606/278
(58) Field of Classification Search ............ 606/60–62, 606/69, 72–73, 151, 54, 59, 277, 278; 248/74.1; 292/74.1; 439/781, 787, 789, 812, 822
See application file for complete search history.

(56) References Cited

U.S. PATENT DOCUMENTS

| | | | | |
|---|---|---|---|---|
| 2,212,156 A | * | 8/1940 | Erdley | 248/229.13 |
| 2,269,790 A | * | 1/1942 | Sherrill | 24/132 R |
| 3,845,523 A | * | 11/1974 | Mayberry | 24/134 P |
| 4,211,380 A | * | 7/1980 | Lillegard et al. | 248/229.15 |
| 4,611,582 A | * | 9/1986 | Duff | 606/61 |
| 5,005,562 A | | 4/1991 | Cotrel | |
| 5,147,360 A | | 9/1992 | Dubousset | |
| 5,275,600 A | | 1/1994 | Allard et al. | |
| 5,415,659 A | * | 5/1995 | Lee et al. | 606/61 |
| 5,423,857 A | * | 6/1995 | Rosenman et al. | 606/219 |
| 5,569,246 A | * | 10/1996 | Ojima et al. | 606/252 |
| 5,601,552 A | * | 2/1997 | Cotrel | 606/250 |
| 5,609,599 A | * | 3/1997 | Levin | 606/153 |
| 5,624,442 A | | 4/1997 | Mellinger et al. | |
| 5,667,526 A | * | 9/1997 | Levin | 606/207 |

(Continued)

FOREIGN PATENT DOCUMENTS

FR    2 736 535    7/1995

(Continued)

*Primary Examiner*—Thomas C Barrett
*Assistant Examiner*—Nicholas Woodall
(74) *Attorney, Agent, or Firm*—Gordon & Jacobson, PC

(57) ABSTRACT

A system for connecting a spinal osteosynthesis rod and a crossbar include a passage for receiving the crossbar and hinge mounted jaws for clamping the rod. A locking device biases the crossbar against the jaws. A return spring pulls the jaws relatively close to one another independently of the crossbar such that the jaws may clamp the osteosynthesis rod to ensure a stable mounting of the connection system to the osteosynthesis rod.

9 Claims, 3 Drawing Sheets

U.S. PATENT DOCUMENTS

| | | | |
|---|---|---|---|
| 5,725,539 A * | 3/1998 | Matern | 606/151 |
| 5,800,548 A | 9/1998 | Martin et al. | |
| 5,968,054 A * | 10/1999 | Yeatts et al. | 606/120 |
| 6,117,136 A * | 9/2000 | Von Strempel | 606/61 |
| 6,193,732 B1 * | 2/2001 | Frantzen et al. | 606/151 |
| 6,368,320 B1 | 4/2002 | Le Couedic et al. | |
| 6,602,253 B2 * | 8/2003 | Richelsoph et al. | 606/61 |
| 6,749,613 B1 * | 6/2004 | Conchy et al. | 606/61 |
| 2004/0092931 A1 * | 5/2004 | Taylor et al. | 606/61 |

FOREIGN PATENT DOCUMENTS

| | | |
|---|---|---|
| FR | 2 745 708 | 3/1996 |
| FR | 2 771 918 | 12/1997 |

* cited by examiner

CONNECTION SYSTEM BETWEEN A SPINAL ROD AND A TRANSVERSE BAR

CROSS-REFERENCE TO RELATED APPLICATIONS

This application claims the benefit of International Application No. PCT/FR03/00425 filed Feb. 11, 2003, which claims priority to French Application No. 02/01626 filed Feb. 11, 2002 both of which are hereby incorporated herein in their entireties by reference.

FIELD OF THE INVENTION

This invention concerns the technical area of osteosynthesis in the general sense and covers, in particular, devices that permit an intervertebral connection capable of stabilizing the spine or correcting deformations of the spinal column.

BACKGROUND OF THE INVENTION

This invention more particularly covers the area of systems capable of providing a connection between a spinal osteosynthesis rod and a crossbar.

In the state of the art, there are a number of known intervertebral connecting devices. In a conventional way, such a device includes bone anchoring elements such as, for example, peduncular implantation screws or vertebral hooks, each equipped with an attachment head for a connection rod joining these elements together. The bone anchorage elements are distributed along the area of the spinal column to be treated to permit the mounting of two connection shafts extending more or less in parallel to one another on either side of the spinal apophyses of the vertebrae. At least one cross strut between the connection rods is advantageously used to stabilize and/or achieve a corrective effect on the arrangement made (either in relaxation or in compression).

Different types of connection systems between an osteosynthesis rod and a crossbar have been proposed in the prior art. For example patent FR 2 745 708 describes a connection system consisting of a first jaw-shaped part with a channel for the crossbar and a lock screw that can extend into the channel, and a second part in the form of an opposing jaw hinged onto the first part. The channel is adapted to receive the transversal connection part which, when the screw is tightened, can come to rest against the first and second parts in order to bring the jaws together. Such a connection system has the advantage of being able to be adapted directly to spinal osteosynthesis rods at any point on the rods, except of course the installation sites of the peduncular screws and hooks. Moreover, the jaws of this system partially surround the osteosynthesis rod, which prevents local intervention on the vertebrae to clear the space needed to install this connection system.

However, it must be noted that the operation of installing this system connecting a crossbar and an osteosynthesis rod is very difficult to carry out properly. Indeed, one must recognize that the connecting system must be maintained on the osteosynthesis rod while making sure the crossbar slides through the reception channel. Maintenance of the system must be pursued in order to permit a slight tightening of the lock screw to make sure the connection system remains in position while retaining overall mobility in order to install another connection system at the opposite end of the crossbar.

To try to offset these drawbacks, document FR 2 771 918 proposed a connector for a spinal osteosynthesis device made in the form of a single piece designed to present two jaws extending by means of connections from a head for a crossbar to pass. Given the elasticity of the material and the slots made at the connections, the two jaws rotate freely to tighten the osteosynthesis rod. This connector is therefore clamped onto the rod before the crossbar is installed. However, the connector is adapted to the rod with a clamping force that is difficult to control given the way the jaws are made. It is therefore difficult to install and position the connector on the rod.

To achieve this objective, the connection system between a spinal osteosynthesis rod and a crossbar is set up in such a way as to offer a channel for the crossbar that is designed to exert an effort on two jaws hinge-mounted so as to make sure they will come together when a locking device is tightened. According to the invention, the connection system includes a common hinge pin to which the jaws are attached and a return spring mounted so as to work on the two jaws to bring them relatively close together independently of the crossbar in such a way that the jaws clamp the osteosynthesis rod in order to ensure the stable mounting of the connection system onto the said rod.

SUMMARY OF THE INVENTION

According to a preferred embodiment of the invention, the connection system includes a means for limiting how close the jaws come toward one another under the action of the return spring so that they form between them, when they are the closest to one another a coupling channel for the osteosynthesis rod such that when a thrusting effort is applied to the jaws when in the rest position on the osteosynthesis rod, the jaws open to enclose and clamp onto the rod so that the connection system is fastened to the rod.

A number of other characteristics emerge from the description given above with reference to the attached drawings which show, as non-limiting examples, some forms of embodiment and implementation of the object of the invention.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternate embodiments.

Figure 1:
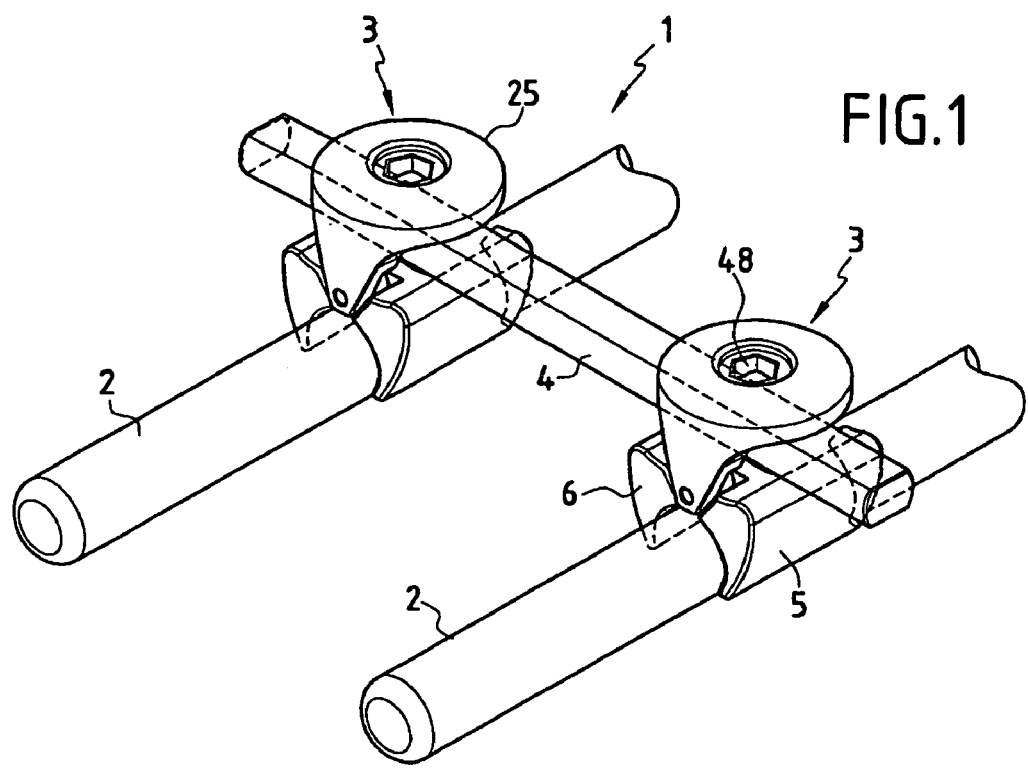
FIG. 1 is a partial perspective view showing a spinal connection device equipped with connection systems according to the invention.

Referring initially to FIG. 1, FIG. 1 is a partial representation of an intervertebral connection device 1 including two spinal osteosynthesis rods 2 each of which has a circular cross-section and is designed to be fastened onto vertebrae by means of bone anchorage elements not shown but known in themselves, such as peduncular screws or hooks.

The purpose of the invention is a connecting system 3 between the osteosynthesis rod 2 and a crossbar 4 which has, for example, a rectangular cross-section. In the example illustrated, the crossbar 4 is intended to provide bracing between the two osteosynthesis rods 2 such that each end of the crossbar 4 is assembled to a rod 2 through a connection system 3 according to the invention.

Figure 3:
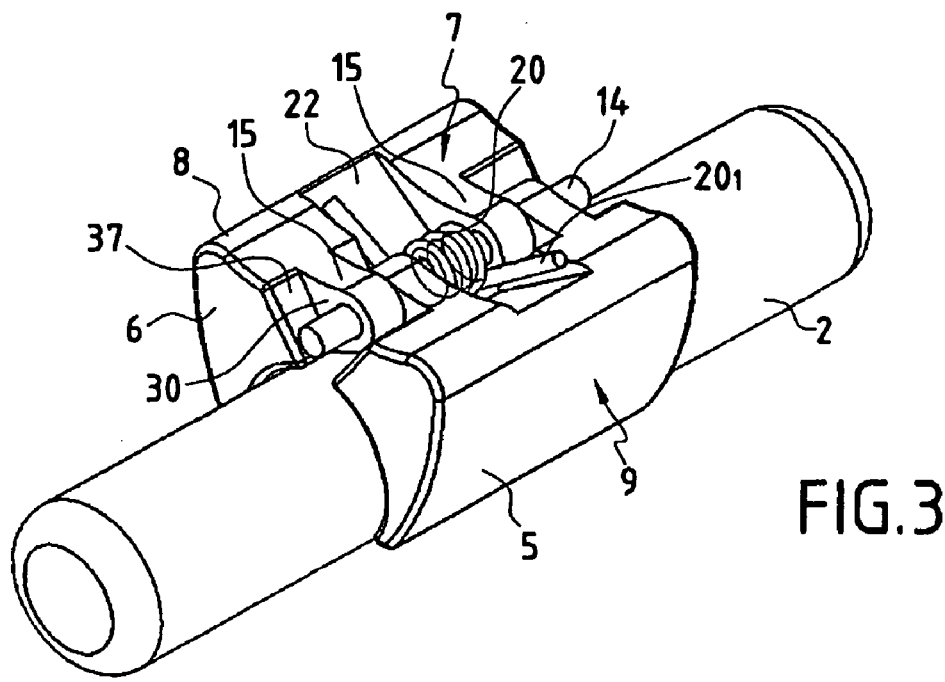
FIG. 3 is a perspective of a connection system according to the invention, from which a portion has been torn away.
Figure 4:
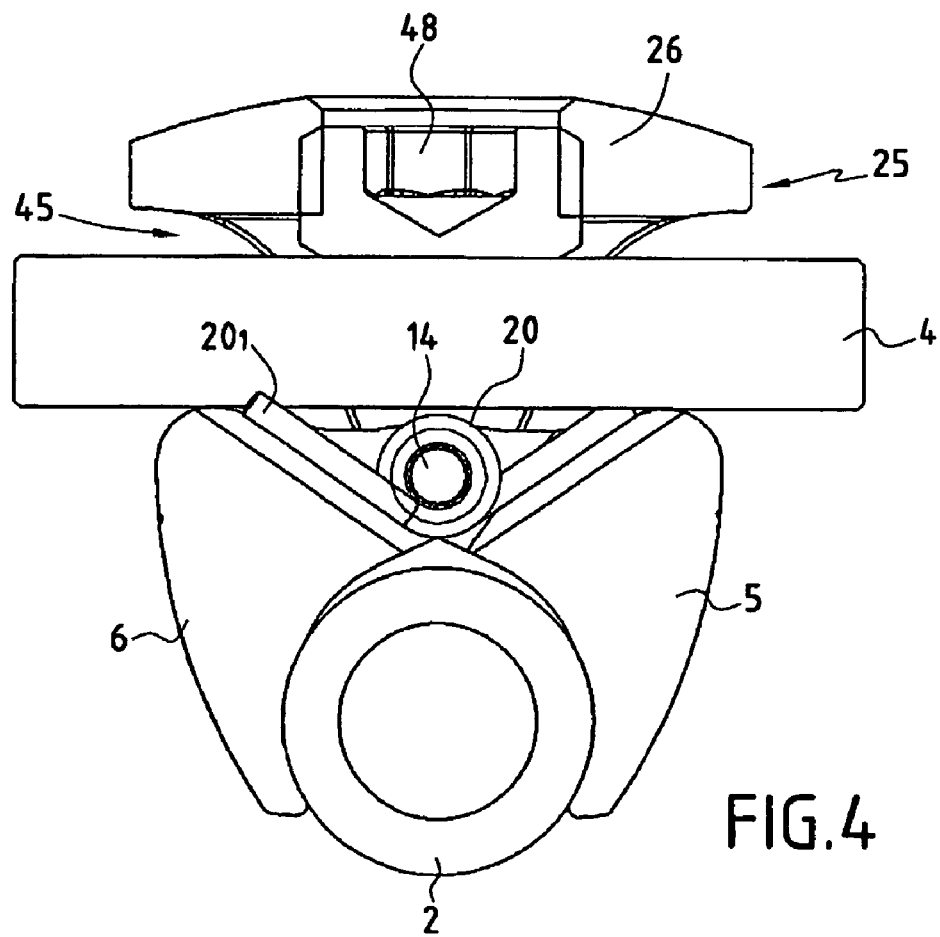
FIG. 4 is a front view showing the connection system between an osteosynthesis rod and a crossbar.

The connection system 3 according to the invention includes a first jaw 5 and a second jaw 6 opposing the first jaw forming a clamp or clip intended to be mounted onto an osteosynthesis rod 2. As more precisely shown in FIGS. 2 to 4, each jaw, 5, 6 has a general profile that can be assimilated to a triangle. Thus, each jaw 5, 6 has a support plate 7, extending to the outside through a groove 8 connecting to a convex outer surface 9. Each jaw 5, 6 also includes a clamping surface 11 with a concave profile that is connected to the outer surface 9 by one extreme edge 12. Each jaw 5, 6 therefore has a tapered profile that limits its size.

The jaws 5, 6, which are made of two separate parts, are hinge-mounted onto a common hinge pin 14 and are turned to face one another. To that end, each jaw 5, 6 has a pair of brackets 15 each one having a hole in it to allow passage of the common hinge pin 14. The pairs of brackets 15 are installed at the level of a connecting zone 16 between the clamping surface 11 and the support plate 7. The pair of brackets 15 of one jaw extends symmetrically with respect to the pair of brackets of the other jaw. In addition, the pairs of brackets 15 protrude from the connection zone 16 of the jaws in such a way as to be interpenetrated in order to permit alignment of the holes through which the hinge pin 14 passes.

According to one characteristic of the invention, the connection system 3 includes at least one return spring 20 that pulls the jaws 5, 6 toward one another in a relative way, in other words, so they can close so that the jaws 5, 6 will clamp onto the osteosynthesis rod 2 in order to ensure the stable installation of the connection system on said rod 2. The return spring 20 is a part separate or independent of the jaws 5, 6 and is mounted in such a way as to press on the two jaws 5, 6 in order to bring them relatively closer to one another. In the example illustrated, the return spring 20 consists of a coil spring engaged on the hinge pin 14, each of whose ends $20_1$ rests in a notch 22 made from the support plates 7 of the jaws. The return spring 20 is therefore seated between the two jaws 5, 6 in the notch 22 created between the two jaws. Of course, the return spring 20 could be made in a different manner, for example, in the form of a leaf spring.

To the extent the jaws 5, 6 are symmetrical with respect to the hinge pin 14, the tightening effort exerted on the rod by the jaws is symmetrically opposed by being extended to the two opposing surfaces of this rod. It must be recognized that this clamp or clip formed by the two jaws 5, 6 is capable of being installed on rods that have diameters of different values while effectively clamping the rod. According to a preferred exemplified embodiment, the clamping surface 11 of each jaw 5, 6 consists of bearing surfaces $11_1$ and $11_2$ of different cross-sections in order to improve the surface contact with the rod in terms of the diameter of the rods 2. It should be noted that the dimensioning of the jaws 5, 6 is adapted so that when in clamping position on the rod 2, their outside edges 12 are at all times set back with respect to a plane passing through the external generatrix of the rod 2. The jaws 5, 6 thus partially surround the rod 2.

The connection system 3 also includes a mounting support 25 for the jaws 5, 6. As more clearly appears in FIGS. 1 and 2, the support 25 is in the form of a caliper comprising a cap 26 extended on both sides by jamb 27 at each end of which there is a borehole 28 to receive one end of the hinge pin 14. The jambs 27 and the jaws 5, 6 are designed so as to permit the movement of the jaws so they can clamp onto the rod 2. To that end, each jaw 5, 6 has at the level of its area of connection 16, a clearance channel 30 created starting from the support plate 7 and opening onto the side faces of the jaws.

Figure 2:
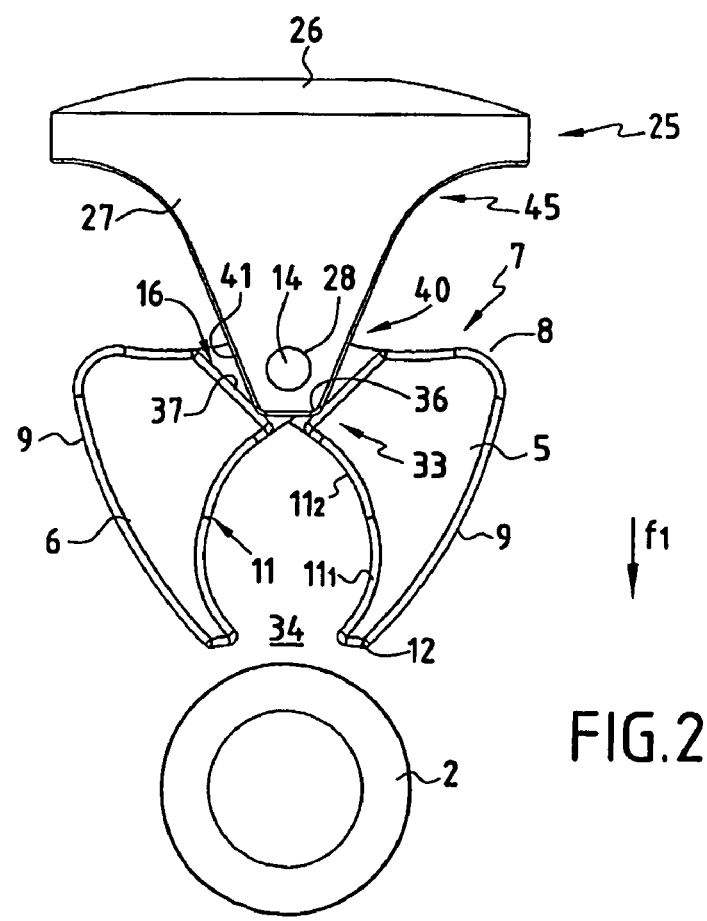
FIG. 2 is a front view of a connection system according to the invention.

According to a preferred exemplified embodiment, the connection system 3 includes a means 33 for limiting how close the jaws 5, 6 come together under the action of the return spring so that they will form between them, when they are closest to one another, as shown in FIG. 2, a channel 34 for engagement of the osteosynthesis rod 2 so that when a thrusting effort is exerted on the jaws resting on the rod 2, the jaws open to enclose and clamp onto the rod. When they are in this position of maximum closeness, the outside edges 12 of the jaws are separated so as to permit the gradual opening of the jaws so that the rod 2 can be engaged between the jaws 5, 6 where it will be clamped and the connection system 3 will be fastened onto the rod.

In the exemplified embodiment illustrated, the means for limiting how close the jaws come together 33 consists of stops 36 created by the edge of the jambs 27 on which a back wall 37, limiting the clearance 30, comes to rest. It is clear that the jaws 5, 6 in rest position are worked on by the return spring 20 until they are as close as possible, this position corresponding to the resting of the jaws 5, 6 against the stops 36.

According to another preferred exemplified embodiment, the connection system 3 includes a means 40 for limiting the separation of the jaws 5, 6 under the action, in particular, of an untimely separating effort of the jaws 5, 6 in order to prevent damage to the return spring 20. This means of limiting the separation 40 consists of the edge 41 of the jambs 27 on which the back wall 37 of the jaws can come in contact. The connection system 3 also includes a passage 45 for the crossbar 4. In the exemplified embodiment illustrated in the drawings, the passage 45 is delimited in part by the support 25, in other words by the internal faces of the jambs 27 and of the cap 26 and by the support plate 7 of the jaws. This passage 45 includes a rectangular cross-section oriented along an axis substantially orthogonal to the hinge pin 14 of the jaws 5, 6.

Figure 5:
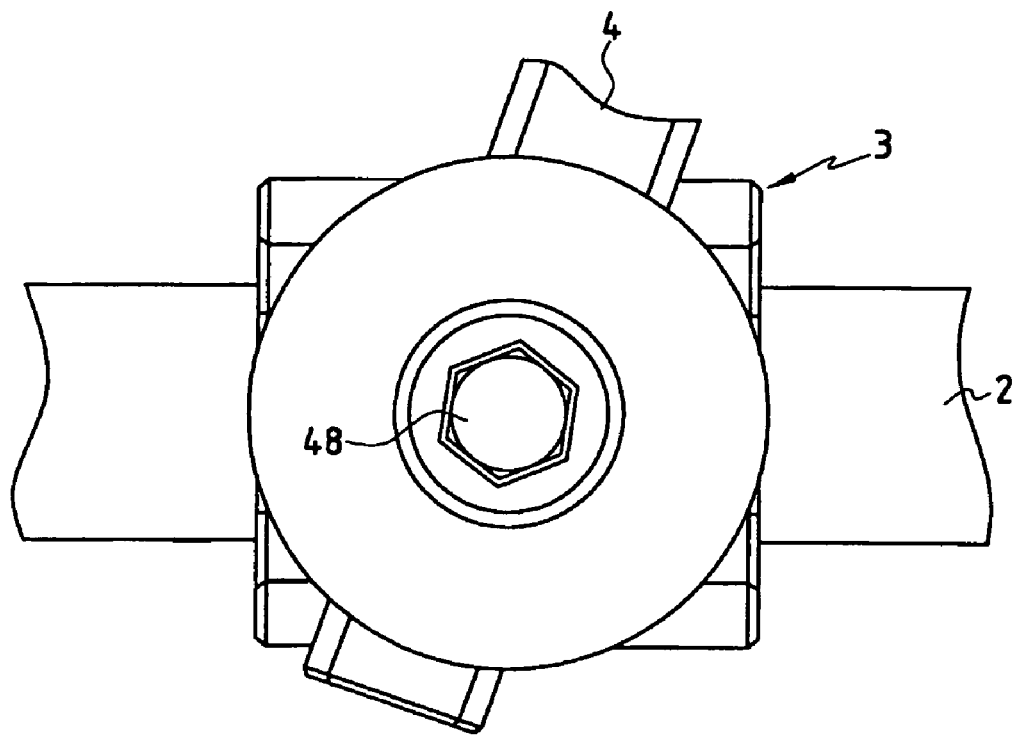
FIG. 5 is a top view of a connection system according to the invention.

The connection system 3 also includes a clamping device 48 such as a screw that extends inside the passage 45. This lock screw 48 is screwed into an internal screw thread on the cap 26 in such a way as to be accessible from the outside face of the cap 26 (FIG. 5).

The implementation of a connection system 3 between an osteosynthesis rod 2 and a crossbar 4 flows directly from the preceding description.

After the installation of a spinal osteosynthesis rod according to known techniques, the connection system 3 can be stably assembled to said rod 2 at the desired point. In that connection, the connection system, generally without the crossbar 4, is shifted by means of a specially-adapted ancillary device, in a direction substantially perpendicular to the axis of the rod, by orienting the extreme edges 12 of the jaws toward the osteosynthesis rod 2. As more specifically indicated in FIG. 2, the connection system 3 is moved in the direction of the arrow $f_1$. During this movement, the jaws 5, 6 rest on the rod 2 in such a way that pursuing the thrusting effort in the direction $f_1$ leads to the gradual opening up of the jaws which then enclose and clamp onto this rod. It should be noted that the opening of the jaws 5, 6 occurs automatically and easily due to the presence of the clearance channel 34 made between the outside edges 12 of the jaws. After elimination of the thrusting effort, the jaws 5, 6 exert, under the action of the return spring 20, sufficient clamping effort around the rod 2 to permit it to be stably mounted onto the rod 2 without outside intervention.

The stable positioning of such a connection system 3 onto the rod 2 facilitates the subsequent operation of inserting the crossbar 4 into the passage 45. Of course, in the event a crossbar 4 is placed between two osteosynthesis rods 2, an identical operation involving the mounting of a connection system 3 pursuant to the invention is carried out on the other osteosynthesis rod. As more precisely illustrated in FIG. 5, it should be noted that the width of the passage 45 is greater than the width of the bar 4 to permit the angular clearance of the bar with respect to the rod 2.

After the positioning of the crossbar 4, the locking screw 48 is screwed in such a way that the bar 4 rests on the jaws 5, 6 in order to bring them together so as to permit the rod 2 to be clamped by the jaws 5, 6. To that end, the connecting grooves 8 of the support plates extend to a higher level with respect to the hinge pin 14, making it possible for the bar to rest on these areas and then for the jaws 5, 6 to pivot toward one another.

Figure 6:
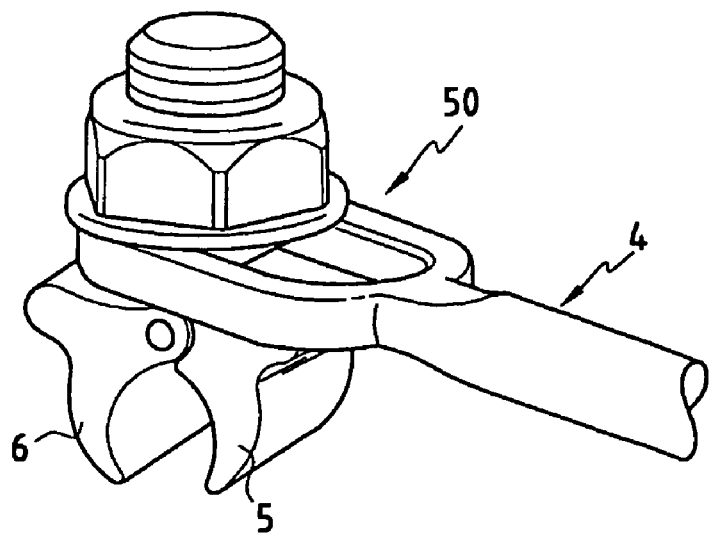
FIG. 6 is a perspective of another variant form of embodiment of a connection system according to the invention.

In the example illustrated in FIGS. 1 to 5, the crossbar 4 exerts a direct effort on the jaws 5, 6 under the action of the locking screw 48. FIG. 6 shows another form of embodiment in which the bar 4 is equipped with an opening 50 that is in contact on the support plates 7 of the jaws, which is acted upon by a locking device consisting of a nut fitted onto a threaded rod on the support 25. It should be noted that the effort transmitted by the bar 4 to the jaws 5, 6 can be exerted indirectly through a washer placed between the jaws and the bar 4.

The invention is not limited to the examples described and represented, as various modifications can be made to same without departing from its context.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An intervertebral connection system for stabilizing the spine of a patient, comprising:

a first connecting device comprising a support having a first channel for receiving a crossbar therein; opposing jaws hingedly mounted to the support by a common hinge pin for receiving a first osteosynthesis rod therebetween, each jaw including a clamping surface constructed and arranged for clamping the first osteosynthesis rod, and a supporting surface arranged for supporting a crossbar within the first channel in a direction transverse to the first osteosynthesis rod;

a return spring mounted so as to bias the jaws closer to one another independently of the crossbar, wherein the jaws clamp the first osteosynthesis rod for ensuring a stable mounting of the connection system onto the first osteosynthesis rod; and a locking device operable with the support for biasing the crossbar against the supporting surface of the jaws for clamping the rod therewith;

a second connecting device comprising a support having a second channel for receiving a crossbar therein;

opposing jaws hingedly mounted to the support by a common hinge pin for receiving a second osteosynthesis rod therebetween, each jaw including a clamping surface constructed and arranged for clamping the second osteosynthesis rod, and a supporting surface arranged for supporting a crossbar within the channel in a direction transverse to the second osteosynthesis rod;

a return spring mounted so as to bias the jaws closer to one another independently of the crossbar, wherein the jaws clamp the second osteosynthesis rod for ensuring a stable mounting of the connection system onto the osteosynthesis rod; and a locking device operable with the support for biasing the crossbar against the supporting surface of the jaws for clamping the rod therewith; and a crossbar transverse to the first and second osteosynthesis rods and received within the first and second channels and biased by the locking means of the first connecting device and the second connecting device against the supporting surfaces of the first connecting device and the second connecting device, respectively.

2. A system for connecting a spinal osteosynthesis rod and a crossbar, the system comprising:

a support;

opposing symmetrical jaws hingedly mounted to the support by a common hinge pin for receiving an osteosynthesis rod therebetween, each jaw including a clamping surface constructed and arranged for clamping together on the osteosynthesis rod, the clamping surface including a plurality of bearing surfaces with differing cross-sections, the jaws able to be mounted on a plurality of osteosynthesis rods of differing diameters, and each jaw including a supporting surface defining with the support, a channel therebetween arranged for supporting a crossbar within the channel in a direction transverse to the osteosynthesis rod;

a return spring mounted so as to bias the jaws closer to one another independently of the crossbar, wherein the jaws clamp the osteosynthesis rod for ensuring a stable mounting of the connection system onto the osteosynthesis rod;

a locking device operable with the support for biasing the crossbar against the supporting surface of the jaws for clamping the rod therewith, and means for limiting how close the jaws are brought together by action of the return spring such as to form between the jaws, when they are as close as possible, an engagement channel for the osteosynthesis rod such that when a thrusting effort is applied to the jaws when supported on the osteosynthesis rod, the jaws open up to enclose and clamp the osteosynthesis rod so that the connection system is attached thereto.

3. A system according to claim 2, wherein the return spring is engaged onto the hinge pin while lodged in a notch formed in the jaws.

4. A system according to claim 2, further comprising stops operable with the jaws for limiting a space therebetween.

5. A system according to claim 2, further comprising at least one crossbar carried by the support for connecting to at least one osteosynthesis rod clamped by the jaws.

6. A system for connecting a spinal osteosynthesis rod and a crossbar, the system comprising:

a support;

a hinge pin carried by the support;

opposing symmetrical jaws hingedly mounted to the support by the hinge pin for receiving an osteosynthesis rod therebetween, each jaw including a clamping surface constructed and arranged for clamping together on the osteosynthesis rod, and a supporting surface defining with the support, a channel therebetween forming a passage for supporting a crossbar, the passage extending in a direction substantially perpendicular to the hinge pin and transverse to the osteosynthesis rod, said passage having a width greater than a width dimension of the crossbar for permitting angular clearance for the crossbar within the channel in a direction;

a return spring mounted so as to bias the jaws closer to one another independently of the crossbar, wherein the jaws clamp the osteosynthesis rod for ensuring a stable mounting of the connection system onto the osteosynthesis rod;

a locking device operable with the support and extending into the passage for biasing the crossbar against the supporting surface of the jaws for clamping the rod therewith, and means for limiting how close the jaws are brought together by action of the return spring such as to form between the jaws, when they are as close as possible, an engagement channel for the osteosynthesis rod such that when a thrusting effort is applied to the jaws when supported on the osteosynthesis rod, the jaws open up to enclose and clamp the osteosynthesis rod so that the connection system is attached thereto.

7. A system according to claim 6, wherein the return spring is engaged onto the hinge pin while lodged in a notch formed in the jaws.

8. A system according to claim 6, further comprising stops operable with the jaws for limiting a space therebetween.

9. A system according to claim 6, further comprising at least one crossbar carried by the support for connecting to at least one osteosynthesis rod clamped by the jaws.

* * * * *